(12) United States Patent
Nishikawa et al.

(10) Patent No.: US 6,342,377 B1
(45) Date of Patent: Jan. 29, 2002

(54) MICROORGANISMS PRODUCING 5-AMINOLEVULINIC ACID AND PROCESSES FOR PRODUCING 5-AMINOLEVULINIC ACID BY USING THE SAME

(75) Inventors: Seiji Nishikawa; Tohru Tanaka; Tomomi Kaminaga, all of Saitama; Kikuo Watanabe, deceased, late of Saitama, by Kiichi Watanabe, Chiyo Watanabe, legal heirs; Nobuya Miyachi, Saitama; Keitaro Watanabe, Saitama; Yasushi Hotta, Saitama, all of (JP)

(73) Assignees: Cosmo Research Intitute; Cosmo Oil Co., Ltd., both of Tokyo (JP)

( * ) Notice: Subject to any disclaimer, the term of this patent is extended or adjusted under 35 U.S.C. 154(b) by 0 days.

(21) Appl. No.: 09/424,671
(22) PCT Filed: May 27, 1998
(86) PCT No.: PCT/JP98/02321
  § 371 Date: Feb. 28, 2000
  § 102(e) Date: Feb. 28, 2000
(87) PCT Pub. No.: WO98/54297
  PCT Pub. Date: Dec. 3, 1998

(30) Foreign Application Priority Data

May 27, 1997 (JP) .............................. 9-136548

(51) Int. Cl.$^7$ .......................... C12P 13/00; C12N 1/20
(52) U.S. Cl. ................. 435/128; 435/252.1; 435/252.3
(58) Field of Search ............................. 435/128, 252.3, 435/252.1

(56) References Cited

U.S. PATENT DOCUMENTS 5,733,770 A * 3/1998 Watanabe et al. ............ 435/128
5,763,235 A * 6/1998 Watanabe et al. ............ 435/128

FOREIGN PATENT DOCUMENTS

| JP | 5-95782 | 4/1993 | ............ C12N/1/20 |
| JP | 6-169758 | 6/1994 | ............ C12N/1/20 |
| JP | 8-168391 | 7/1996 | ............ C12P/13/00 |

OTHER PUBLICATIONS

Ken Sasaki et al, Influence of Iron on the Excretion of 5–Aminolevulinic Acid by a Photosynthetic Bacterium *Rhodobacter sphaeroides*, 1989, vol. 68, No. 5, pp. 378–381.

Ellen L. Neidle et al, 5–Aminolevulinic Acid Availability and control of Spectral Complex Formation in HemA and HemT Mutants of *Rhodobacter sphaeroides*, Apr. 1993, vol. 175, pp. 2304–2313.

* cited by examiner

Primary Examiner—Herbert J. Lilling
(74) Attorney, Agent, or Firm—Sughrue Mion, PLLC

(57) ABSTRACT

Microorganisms producing 5-aminolevulinic acid which show a 5-aminolevulinic acid synthetase activity of 2 to 7 (nmol/min/mg protein) under aerobic culture conditions with a dissolved oxygen concentration of 0.70 to 6.60 ppm; a process for producing 5-aminolevulinic acid characterized by culturing one or more microorganisms and harvesting 5-aminolevulinic acid from the obtained culture; a process for producing 5-aminolevulinic acid characterized by culturing 5-aminolevulinic acid-producing microorganisms in a medium containing 5 to 500 $\mu$M of iron components; and a method for culturing 5-aminolevulinic acid-producing microorganisms.

10 Claims, 1 Drawing Sheet

MICROORGANISMS PRODUCING 5-AMINOLEVULINIC ACID AND PROCESSES FOR PRODUCING 5-AMINOLEVULINIC ACID BY USING THE SAME

TECHNICAL FIELD

The present invention relates to a microorganism which produces and accumulates 5-aminolevulinic acid at a high concentration, and to a process for producing 5-aminolevulinic acid using the same.

BACKGROUND ART

5-Aminolevulinic acid is a compound which is broadly present in the biosphere as a precursor of tetrapyrrole compounds and takes important roles in vivo. 5-Aminolevulinic acid is a natural compound which shows excellent functions as, for example, herbicides, insecticides, plant growth regulators, plant photosynthesis reinforcing agents, and the like, and also has advantageous characteristics such as no toxicity upon humans and animals and no residual property in the environment due to its high decomposability (e.g., see JP-A-61-502814, JP-A-2-138201 etc.).

However, 5-aminolevulinic acid has a problem in that it lacks in practicability for use in the above uses because of its high production cost (*CHEMICAL WEEK*, Oct., 29 (1984)).

Accordingly, many chemical synthesis processes have been examined (e.g., see JP-A-2-76841), but satisfactory processes have not been developed yet.

On the other hand, other processes for producing 5-aminolevulinic acid have also been examined using microorganisms belonging to the genus Rhodobacterium, the genus Propionibacterium, the genus Methanobacterium, the genus Methanosarcina, and the like. However, the processes using microorganisms belonging to the genus Propionibacterium, the genus Methanobacterium, the genus Methanosarcina and the like (e.g., see JP-A-5-184376) are not satisfactory because the production yield is very low.

It is known that purple non-sulfur bacteria, such as microorganisms belonging to the genus Rhodobacterium, and the genus Rhodopseudomonas, and the like, have high ability to synthesize tetrapyrrole compounds using 5-aminolevulinic acid as a metabolic intermediate. However, the use of these microorganisms has a problem in that the produced 5-aminolevulinic acid is metabolized into tetrapyrrole compounds so that a desired amount of 5-aminolevulinic acid is not accumulated.

Thus, since biosynthesis of 5-aminolevulinic acid is regulated in a complicated manner in vivo, it is not easy to obtain a strain capable of accumulating 5-aminolevulinic acid at a high concentration.

On the other hand, a method using a mutant strain of the genus Rhodobacterium capable of accumulating 5-aminolevulinic acid at a maximum amount of 14.3 mM in which glucose is used as a carbon source has been proposed (JP-A-8-168391). However, this method cannot be considered as an industrially advantageous method because it is necessary to keep a dissolved oxygen concentration at a low level during culturing so that aeration in the culture vessel must be carried out by feeding a mixture of air and a nitrogen gas.

Also, this method requires oxygen when 5-aminolevulinic acid is aerobically accumulated using glucose as the carbon source. As a consequence, there is a possibility that 5-aminolevulinic acid is produced efficiently even under conditions that oxygen is present sufficiently because the dissolved oxygen concentration is reduced due to consumption of oxygen by the microorganism. However, it is not possible to produce 5-aminolevulinic acid efficiently under relatively high dissolved oxygen concentration conditions.

DISCLOSURE OF THE INVENTION

An object of the present invention is to provide a microorganism which can produce 5-aminolevulinic acid efficiently even under conditions that a dissolved oxygen concentration is relatively high without requiring feeding of a nitrogen gas or the like. Another object of the present invention is to provide a process for producing 5-aminolevulinic acid using the microorganism.

Under the above conditions, the inventors of the present invention have conducted intensive studies with the aim of obtaining a microorganism capable of producing 5-aminolevulinic acid efficiently and, as a result, found a process for selecting 5-aminolevulinic acid accumulating microorganisms having high productivity and then, using this method, found a microorganism capable of accumulating 5-aminolevulinic acid at a high concentration even with a relatively high dissolved oxygen concentration. Thus the present invention has been accomplished.

Also, the present inventors have developed a markedly efficient process for selecting of 5-aminolevulinic acid accumulating microorganisms which can evaluate a large number of mutant strains by appropriately changing saccharides, glycine, levulinic acid, and the like, and a repeated mutant treatment has become possible. Thus, the present inventors have succeeded in breeding a strain capable of accumulating 5-aminolevulinic acid at a high concentration. Thereafter, the present invention was completed by establishing a culturing process in which saccharides, glycine, levulinic acid, iron components, and the like are appropriately added, and dissolved oxygen and oxidation-reduction potential in the culture broth are controlled.

That is, the present invention provides a 5-aminolevulinic acid-producing microorganism having a 5-aminolevulinate synthase activity of from 2 to 7 (nmol/min/mg protein) under aerobic culturing conditions at a dissolved oxygen concentration of from 0.70 to 6.60 ppm.

Also, the present invention provides a process for producing 5-aminolevulinic acid, comprising culturing at least one of such 5-aminolevulinic acid producing microorganisms and recovering 5-aminolevulinic acid from the resulting culture.

Furthermore, the present invention provides a process for producing 5-aminolevulinic acid, comprising culturing a 5-aminolevulinic acid-producing microorganism in a medium containing an iron component at an amount of from 5 to 500 $\mu$M and recovering 5-aminolevulinic acid from the resulting culture mixture.

Moreover, the present invention provides a process for culturing a 5-aminolevulinic acid-producing microorganism, comprising culturing a 5-aminolevulinic acid producing microorganism in a medium containing an iron component at an amount of from 5 to 500 $\mu$M.

BEST MODE OF CARRYING OUT THE INVENTION

Figure 1:
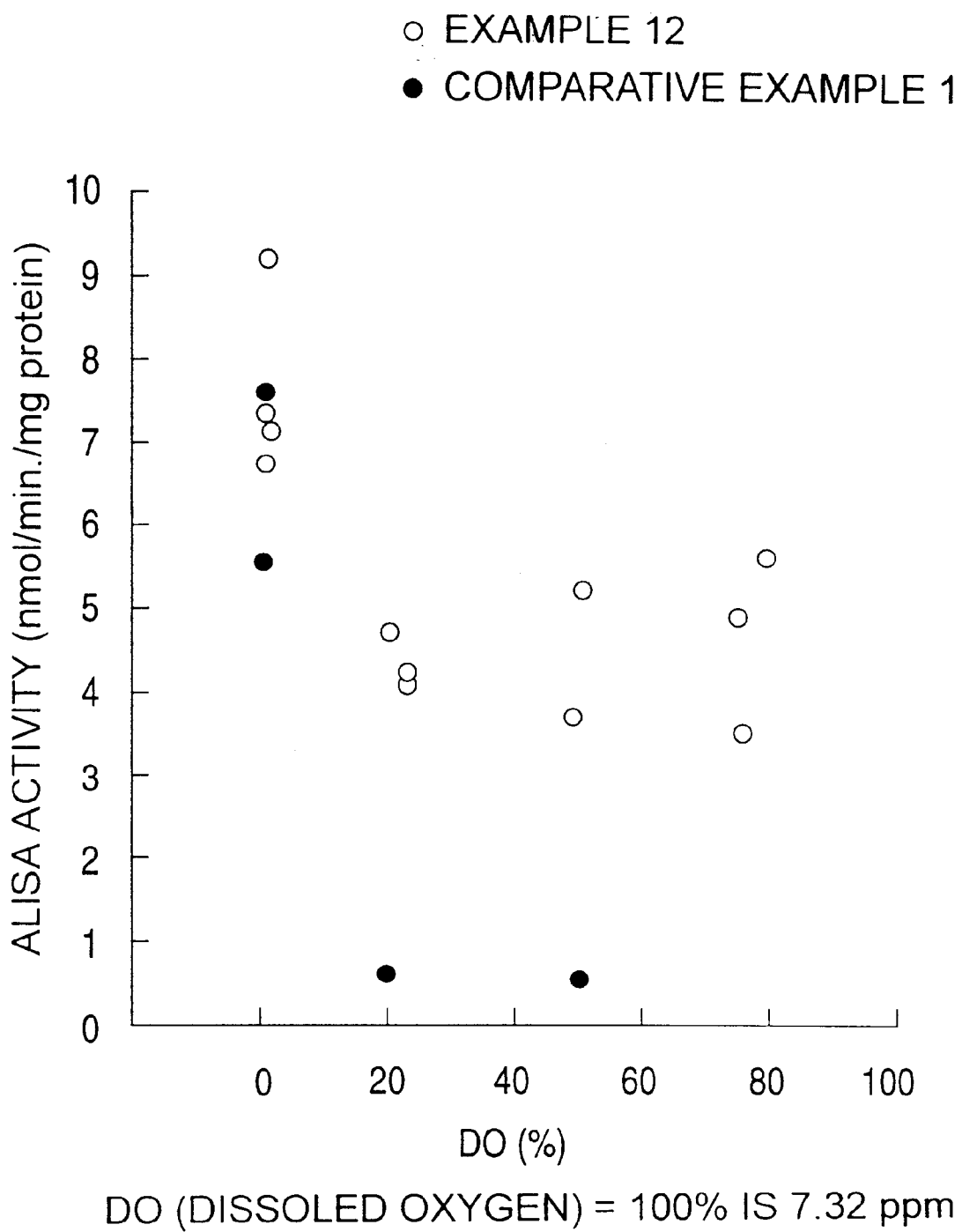
FIG. 1 is a graph showing a relationship between dissolved oxygen and 5-aminolevulinic acid synthase activity.

The 5-aminolevulinic acid producing microorganism of the present invention can be obtained, for example, by using a wild strain or a mutant strain of a purple non-sulfur bacterium as a parent strain, subjecting it to a mutation treatment, and selecting a strain having a 5-aminolevulinate synthase activity of from 2 to 7 (nmol/min/mg protein) under conditions at a dissolved oxygen concentration of from 0.70 to 6.60 ppm, preferably a 5-aminolevulinic acid synthase activity of from 3.5 to 5.6 (nmol/min/mg protein) at a dissolved oxygen concentration of from 1.46 to 5.86 ppm.

Specifically, the following method can be exemplified.

Firstly, a liquid medium in which a parent strain can grow is prepared in a test tube and sterilized, and then the parent strain is inoculated into the medium and cultured under shaking. The thus grown cells are washed with a buffer and subjected to a mutation treatment.

As the mutation treatment, a general mutation means can be employed. Examples thereof include a method in which cells of the parent strain grown on an agar medium are irradiated with a physical mutagen, such as ultraviolet rays, ionizing radiation, or the like, and a method in which the parent strain is cultured in a buffer to which a chemical mutagen including an alkylation agent, such as ethyl methanesulfonate (EMS), N-methyl-N'-nitro-N-nitrosoguanidine (NTG), ethylnitrosourea (ENU) or the like, and a base analog, such as bromodeoxyuridine (BrdUrd), or the like, has been added.

The cells thus treated by the above-described mutation means are washed with a buffer again and spread on an agar medium for culturing. Also, selection of a strain having the above-described properties from the mutant strains thus grown by this culturing is carried out by the following steps.

Each of the thus obtained mutant strains is cultured in a test tube or the like, and levulinic acid and glycine are added thereto after cell growth. After the addition of these compounds, the amount of the accumulated 5-aminolevulinic acid in the culture broth is measured to select a strain having high 5-aminolevulinic acid productivity.

In order to culture and evaluate larger numbers of microorganisms, it is effective and preferred to use a microtiter plate. In addition, the selection can be carried out efficiently when the measurement of 5-aminolevulinic acid is carried out by the Ehrlich reaction because the accumulated amount of 5-aminolevulinic acid can be recognized visually.

The selection is carried out by selecting approximately 1 to 100 strains having high 5-aminolevulinic acid productivity from about 15,000 mutant strains obtained by the first mutation treatment, and then a strain having stable growing ability and productivity is selected from the thus selected strains by subculturing them in test tubes or on agar plates. It is also preferred in this case to use the Ehrlich reaction and a microtiter.

Using the thus obtained strain as the parent strain, the above-described mutation treatment and selection are repeated. As the productivity of 5-aminolevulinic acid increases by the repetition of the mutation, the optimum concentration of levulinic acid to be added changes in some cases, so that it is preferred to change the concentration of levulinic acid to be added appropriately.

The thus obtained strain by repeating the mutation breeding, having the ability to accumulate a considerable amount of 5-aminolevulinic acid under aerobic conditions, has a feature in that one of the 5-aminolevulinic acid metabolism-related enzymes, namely 5-aminolevulinate synthase, is increased. In addition, unlike the case of the wild strains of photosynthetic bacteria of the same genus, inhibition of 5-aminolevulinate synthase activity hardly occurs in the thus obtained mutant strain even under such conditions that the dissolved oxygen concentration in the culture medium exceeds 2 ppm.

Regarding the parent strain for use in the first step in the above-described method, it is preferred to use a wild strain of a purple non-sulfur bacterium or a mutant strain thereof, particularly a strain which shows good growth on an inexpensive carbon source, such as glucose or the like, under aerobic conditions and has high ability to synthesize tetrapyrrole compounds, such as bacteriochlorophyll or the like. Examples of such a preferred strain include those belonging to the genus Rhodobacterium, particularly *Rhodobacter sphaeroides* or a mutant strain thereof, and *Rhodobacter sphaeroides* CR-002 (FERM P-15312) can be exemplified as the preferred parent strain.

Also, preferred examples of the strain obtained by the above-described mutation and selection include those belonging to the genus Rhodobacterium, particularly a mutant strain of *Rhodobacter sphaeroides*, and a specific example is a strain which has been named *Rhodobacter sphaeroides* CR-0072009 and internationally deposited as FERM BP-6320 on Apr. 7, 1998, in National Institute of Bioscience and Human Technology, Agency of Industrial Science and Technology, the Ministry of International Trade and Industry (Higashi 1-1-3, Tsukuba, Ibaraki, Japan). This strain capable of accumulating a considerable amount of 5-aminolevulinic acid has been obtained by repeating mutation and selection of the above-described *Rhodobacter sphaeroides* CR-002.

Since *Rhodobacter sphaeroides* CR-0072009 is a strain obtained by the mutation of *Rhodobacter sphaeroides* CR-002 as described above, most of its bacteriological properties are identical to those of the strain CR-002.

Bacteriological properties of *Rhodobacter sphaeroides* CR-0072009 are described below.

(a) Morphological Characteristics

Size and shape of cell:
0.5×1 to 2.5 µm, rod, several cells linked in the major axis direction Spore: absent (b) Growth on Agar Medium Glossy, reddish brown circular colony on the medium of Table 1

(c) Physiological Properties

Gram staining: −

Reduction of nitrate: +

Oxidase: +

Glucose fermentation: −

Growth range: pH 4.0 to 9.0, 10° C. to 40° C.

(d) Chemotaxonomic Properties

DNA G/C content (mol %): 68

Quinone type: Q-10

Carotenoid:
+(main components; chloroxanthine, methylchloroxanthine)

Bacteriochlorophyll: +

(e) Other Growth Conditions and the Like

Photosynthetic growth:
Very weak in the medium of Table 1. Although its original strain is a photosynthetic bacterium, its ability to carry out photosynthetic growth is reduced.

Assimilation of glucose (aerobic): +

Assimilation of sodium acetate (aerobic): +

5-Aminolevulinate dehydratase activity:
  ⅓ or less in comparison with the original strain (CR-002) by aerobic culturing Production conditions of 5-aminolevulinic acid using the 5-aminolevulinic acid-producing microorganism of the present invention, mainly in the case of the use of *Rhodobacter sphaeroides* CR-0072009, are described below. Regarding the production conditions of 5-aminolevulinic acid, general microorganism culturing conditions can be employed. Examples of the carbon source include saccharides, such as glucose and the like, or acids, such as acetic acid, malic acid, succinic acid, and the like, and saccharides are particularly advantageous from the economical point of view. Examples of the nitrogen source include inorganic nitrogen sources, for example ammonia nitrogen compounds, such as ammonium sulfate, ammonium chloride, and the like, and nitrate nitrogen compounds such as sodium nitrate and the like; and organic nitrogen sources, such as glycine, urea, polypeptone, yeast extract, casamino acid, and the like. Among these, glycine is preferably added for improving the productivity of 5-aminolevulinic acid. The amount added of glycine is preferably within a range of from 10 to 1,000 mM, more preferably from 10 to 400 mM. Also, it is preferred to use glycine in an amount of from 10 to 200 mM per addition and to add this amount several times.

Furthermore, if necessary, other components, such as vitamins, inorganic salts, and the like, may be added to the medium as occasion demands.

It is known that microorganisms belonging to purple non-sulfur bacteria, such as the genus Rhodobacterium, the genus Rhodopseudomonas, and the like generally have 5-aminolevulinate dehydratase which metabolizes produced 5-aminolevulinic acid. However, since the 5-aminolevulinate dehydratase activity is significantly reduced in the strain of the present invention, 5-aminolevulinic acid can be extracellularly accumulated without adding a 5-aminolevulinic acid dehydratase inhibitor, such as levulinic acid, but the addition of a small amount of the inhibitor is effective in improving 5-aminolevulinic acid productivity. In that case, the amount of the inhibitor to be added is preferably within a range of from 0.01 to 20 mM, more preferably from 0.1 to 10 mM. Any culturing conditions can be used so long as *Rhodobacter sphaeroides* CR-0072009 can grow, but generally, preferred conditions are at culturing temperature of from 10 to 40° C., more preferably from 20 to 35° C., and at medium pH of from 4 to 9, more preferably from 5 to 8.

Also, when the medium pH fluctuates during the culturing, it is preferred to adjust to the above-described range with an alkali solution, such as sodium hydroxide, ammonia, sodium hydroxide, or the like, or with an acid, such as hydrochloric acid, sulfuric acid, phosphoric acid, or the like.

Production of 5-aminolevulinic acid can be carried out simultaneously with or independently from the microbial growth. In this case, the microorganism to be used is either growing cells or resting cells, which can be used as such for the production of 5-aminolevulinic acid or after increasing the cell density, for example, by recovering the cells using an apparatus, such as a centrifuge or the like, and then re-suspending the recovered cells in an appropriate solution, such as a medium, a phosphate buffer, or the like.

In order to further improve productivity of 5-aminolevulinic acid, it is preferred to control the dissolved oxygen concentration and the oxidation-reduction potential in the culture broth to the ranges of from 0.001 to 2 ppm and −220 mV to 50 mV, more preferably from 0.001 to 1 ppm and −200 mV to 0 mV, respectively. Examples of the controlling method of this case include a method in which the agitation speed or aeration rate is changed, a method in which respiration of the microorganism is activated by adding saccharides, yeast extract, or the like, and a combination method thereof.

Also, in order to control the dissolved oxygen and the oxidation-reduction potential more stably, it is effective to add an iron component to the medium for the purpose of increasing the growth rate of the microorganism and thereby stabilizing the respiration activity. The iron component used is preferably an iron salt, and the iron valency is not particularly limited. Examples of the iron compound include ferric chloride, iron(III) sulfate, iron citrate and the like. When a natural substance, such as yeast extract, corn steep liquor, or the like, used as a medium component contains an iron component at a necessary amount, it can be used as the iron compound. It is preferred to add the iron component to the medium at an amount of from 5 to 500 $\mu$M as iron. If the amount is smaller than 5 $\mu$M, no effect to accelerate microbial growth or stabilize respiration activity can be obtained, and if the amount is larger than 500 $\mu$M, microbial growth may be inhibited. A concentration of the iron component is preferably from 10 to 300 $\mu$M, more preferably from 20 to 200 $\mu$M. Also, the iron compound may be included in the medium in advance or added at a later stage.

If necessary, the thus produced 5-aminolevulinic acid can be separated and purified by usually used techniques, such as an ion exchange method, a chromatography method, an extraction method, and the like.

EXAMPLES

The present invention is explained below based on Examples. However, they are shown for only illustration, and the present invention is not limited thereto.

Example 1

Into a 21 mm$\phi$ test tube, 10 ml of glutamate/glucose medium (medium 1) shown in Table 1 was poured, sterilized at 121° C. for 15 minutes, and then allowed to stand for cooling. One loopful of *Rhodobacter sphaeroides* CR-002 (FERM P-15312) was inoculated into the medium and cultured under shaking in the dark at 30° C. for 2 days.

Into another 21 mm$\phi$ test tube, 10 ml of medium 1 was poured and sterilized in the same manner as described above. A 0.5 ml portion of the above culture broth was inoculated into the medium and cultured under shaking in the dark at 32° C. for 18 hours.

TABLE 1

|  | g/L (distilled water) |
| --- | --- |
| Sodium glutamate | 3.8 |
| Glucose | 9.0 |
| Disodium hydrogenphosphate | 1.13 |
| Sodium dihydrogenphosphate | 1.07 |
| Ammonium phosphate | 0.8 |
| Magnesium sulfate | 0.2 |
| Calcium chloride | 0.053 |
| Manganese sulfate | $1.2 \times 10^{-3}$ |
| Nicotinic acid | $1.0 \times 10^{-3}$ |
| Biotin | $1.0 \times 10^{-5}$ |
| Thiamin | $1.0 \times 10^{-3}$ |
| Yeast extract | 2.0 |

The culture broth was centrifuged at 3,000×g for 5 minutes for washing, the resulting supernatant was discarded and then the cells were suspended in the same volume of a Tris-maleate buffer (pH 6.0). This washing step was further repeated twice.

Thereafter, the suspension was centrifuged at 3,000×g for 5 minutes, the resulting supernatant was discarded and then the cells were suspended in a Tris-maleate buffer (pH 6.0) containing 100 μg/ml of NTG and statically cultured at room temperature for 80 minutes.

The thus mutagenized cells were washed three times in the same manner as described above and then inoculated into a test tube containing sterilized medium 1 and cultured under shaking in the dark at 32° C. for 2 days.

The thus obtained culture broth was diluted and spread on an agar plate medium prepared by adding 15 g/L of agar to medium 1 and sterilizing the mixture at 121° C. for 15 minutes, and the cells were cultured in the dark at 32° C. for 4 days.

As a result, about 15,000 colonies were obtained.

Next, sterilized medium 1 was poured into sterilized 96 well microtiter plates at 0.2 ml per well, and each of the above-described approximately 15,000 mutant strains was inoculated into the medium.

After culturing under shaking in the dark at 30° C. for 48 hours on a microplate shaker, each of glycine and levulinic acid was added to each well to give a final concentration of 30 mM, followed by culturing under stirring for 24 hours under the same conditions. 5-Aminolevulinic acid in each well was detected as described below (Ehrlich reaction).

(1) The culture broth in each well was transferred into another microtiter plate and mixed with 0.1 ml of a 1 M acetate buffer containing 1% acetylacetone, and the microtiter plate was sealed, incubated at 100° C. for 15 minutes and then rapidly cooled in ice.
(2) Next, 0.1 ml of an acetic acid solution containing 2% p-dimethylaminobenzaldehyde and 16% perchloric acid was added to each well, and the mixture was allowed to stand at room temperature for 15 minutes to observe development of a reddish purple color by the Ehrlich reaction.
(3) Thereafter, a portion of each reaction solution was sampled and subjected to TLC analysis to exclude strains showing a reddish purple color which was not derived from 5-aminolevulinic acid, thereby selecting 6 mutant strains having high productivity of 5-aminolevulinic acid.

Each of the thus obtained 6 strains was cultured in the dark at 30° C. for 48 hours using a test tube containing medium 1, and the resulting culture broth was spread on an agar plate medium having a composition of medium 1 and cultured to form colonies.

Next, sterilized medium 1 was poured into wells of sterilized 96 well microtiter plate at 0.2 ml per well, and each of optionally selected 60 colonies derived from each of the above-described strains was inoculated into the medium.

After culturing under shaking in the dark at 32° C. for 48 hours on a microplate shaker, glycine was added to each well to give a final concentration of 30 mM, and 30, 15 or 1 mM of levulinic acid was added to wells corresponding to 20 colonies of the above-described 60 colonies. Culturing under stirring was continued for 24 hours under the same conditions, and a portion of the culture broth was sampled from each well to examine productivity of 5-aminolevulinic acid and an optimum concentration of levulinic acid by the Ehrlich reaction. This procedure was repeated three times, and one mutant strain having stably higher productivity than CR-002 was isolated using increase in the productivity and variation of the productivity among colonies as indexes. This strain was named CR-150. The optimum concentration of levulinic acid was 30 mM. When the accumulated amount of 5-aminolevulinic acid in the case of the addition of 30 mM levulinic acid was determined by measuring the absorbance of the Ehrlich reaction at 553 nm using a microplate reader, the strain CR-002 showed a productivity of 0.01 mM, while that of the strain CR-150 was 0.1 mM.

Example 2

The same procedure of Example 1 was repeated, except that the strain was changed to CR-150 to thereby obtain about 15,000 mutant strains. By subjecting them to selection tests in the same manner as in Example 1, a mutant strain CR-268 having more improved productivity than CR-150 was obtained. When the accumulated amount of 5-aminolevulinic acid was determined by measuring the absorbance of the Ehrlich reaction at 553 nm using a microplate reader, the strain CR-268 showed a productivity of 0.3 mM.

Example 3

The same procedure of Example 1 was repeated, except that the strain was changed to CR-268 to thereby obtain about 15,000 mutant strains. By subjecting them to selection tests in the same manner as in Example 1, a mutant strain CR-368 having more improved productivity than CR-268 was obtained. When the accumulated amount of 5-aminolevulinic acid was determined by measuring the absorbance of the Ehrlich reaction at 553 nm using a microplate reader, the strain CR-368 showed a productivity of 0.5 mM.

Example 4

The same procedure of Example 1 was repeated, except that the strain was changed to CR-368 to thereby obtain about 15,000 mutant strains. By subjecting them to selection tests in the same manner as in Example 1, a mutant strain CR-405 having more improved productivity than CR-368 was obtained. When the accumulated amount of 5-aminolevulinic acid was determined by measuring the absorbance of the Ehrlich reaction at 553 nm using a microplate reader, the strain CR-405 showed a productivity of 1.0 mM.

Example 5

The same procedure of Example 1 was repeated, except that the strain was changed to CR-405 to thereby obtain about 15,000 mutant strains. By subjecting them to selection tests in the same manner as described in Example 1 except that the amount of levulinic acid to be added was changed to 15 mM, a mutant strain CR-502 having more improved productivity than CR-405 was obtained. When the accumulated amount of 5-aminolevulinic acid was determined by measuring the absorbance of the Ehrlich reaction at 553 nm using a microplate reader, the strain CR-405 showed a productivity of 1.2 mM, while that of the strain CR-502 was 2.1 mM.

Example 6

The same procedure of Example 1 was repeated, except that the strain was changed to CR-502 to thereby obtain about 15,000 mutant strains. By subjecting them to selection tests in the same manner as described in Example 1 except that the amount of levulinic acid to be added was changed to 1 mM, a mutant strain CR-660 having improved productivity in comparison with CR-502 was obtained. When the accumulated amount of 5-aminolevulinic acid was determined by measuring the absorbance of the Ehrlich reaction at 553 nm using a microplate reader, the strain CR-502 showed a productivity of 2.4 mM, while that of the strain CR-660 was 3.3 mM.

Example 7

The same procedure of Example 1 was repeated, except that the strain was changed to CR-660 to thereby obtain about 15,000 mutant strains. By subjecting them to selection tests in the same manner as in Example 1, except that the amount of levulinic acid to be added was changed to 1 mM, mutant strains CR-0072001, CR-0072002 and CR-0072009 having more improved productivity than CR-660 were obtained. When the accumulated amount of 5-aminolevulinic acid was determined by measuring the absorbance of the Ehrlich reaction at 553 nm using a microplate reader, the productivities of strains CR-0072001, CR-0072002 and CR-0072009 were 5.9, 5.6 and 4.6 mM, respectively.

Example 8

Each of the mutant strains CR-0072001, CR-0072002 and CR-0072009 obtained in Example 7 was inoculated into a 500 ml capacity shaking flask containing 200 ml of medium 1 and cultured under shaking in the dark at 32° C. for 48 hours on a reciprocal shaker. After culturing, the resulting cells were recovered by centrifugation at 5,000×g for 10 minutes and suspended in medium 2 shown in Table 2 to give a density of 0.5 g wet cells/10 ml, and 3 ml of the suspension was poured into 21 mm test tubes. Cells in the thus prepared test tubes were cultured under shaking in the dark at 32° C. for 20 hours on a reciprocal shaker, and the amount of 5-aminolevulinic acid in the culture broth was measured by the method of Okayama et al. (*CLINICAL CHEMISTRY*, Vol. 36, No. 8, p. 1494, 1990). As a result, the productivities of strains CR-0072001, CR-0072002 and CR-0072009 were 19.0, 21.5 and 31.0 mM, respectively.

TABLE 2

|  | g/L (distilled water) (pH 6.5) |
| --- | --- |
| Sodium glutamate | 3.8 |
| Glucose | 18.0 |
| Glycine | 9.0 |
| Levulinic acid | 0.116 |
| Disodium hydrogenphosphate | 4.52 |
| Sodium dihydrogenphosphate | 4.35 |
| Ammonium phosphate | 0.8 |
| Magnesium sulfate | 0.2 |
| Calcium chloride | 0.053 |
| Manganese sulfate | $1.2 \times 10^{-3}$ |
| Nicotinic acid | $1.0 \times 10^{-3}$ |
| Biotin | $1.0 \times 10^{-5}$ |
| Thiamin | $1.0 \times 10^{-3}$ |
| Yeast extract | 12.0 |

Example 9

The mutant strain CR-0072009 was inoculated into a 300 ml capacity baffled conical flask containing 50 ml of medium 3 shown in Table 3 and cultured under shaking in the dark at 32° C. for 48 hours on a rotary shaker. The resulting culture broth was inoculated into a 3 L capacity fermentor containing 1.8 L of medium 3 and cultured under shaking at 32° C. at an aeration rate of 0.36 L/min and 400 rpm. After culturing for 40 hours while controlling the medium pH at 6.5 to 6.6 using sulfuric acid and sodium hydroxide, 0.210 g of levulinic acid, 8.1 g of glycine and 18 g of yeast extract (D-3, manufactured by Japan Pharmaceutical) were added to the medium and the culturing was continued by changing the stirring speed to 325 rpm and controlling the medium pH at 6.3 to 6.4 using sulfuric acid and sodium hydroxide. A 8.1 g portion of glycine was added 12, 26 and 38 hours thereafter. The culturing was stopped 50 hours after the addition of levulinic acid. The amount of 5-aminolevulinic acid in the culture broth was 60 mM when measured by the method of Okayama et al. (*CLINICAL, CHEMISTRY*, Vol. 36, No. 8, p. 1494, 1990). The average dissolved oxygen concentration in the culture broth after the addition of levulinic acid was 0.01 ppm. Also, the oxidation-reduction potential in the culture broth after the addition of levulinic acid shifted within the range of from −180 mV to −50 mV.

TABLE 3

|  | g/L (distilled water) (pH 6.8) |
| --- | --- |
| Sodium glutamate | 7.6 |
| Glucose | 36.0 |
| Disodium hydrogenphosphate | 2.26 |
| Sodium dihydrogenphosphate | 2.14 |
| Ammonium phosphate | 1.6 |
| Magnesium sulfate | 0.4 |
| Calcium chloride | 0.106 |
| Manganese sulfate | $2.4 \times 10^{-3}$ |
| Nicotinic acid | $2.0 \times 10^{-3}$ |
| Biotin | $2.0 \times 10^{-5}$ |
| Thiamin | $2.0 \times 10^{-3}$ |
| Yeast extract | 5.0 |

Example 10

The mutant strain CR-0072009 was inoculated into a 300 ml capacity baffled conical flask containing 50 ml of the medium 3 and cultured under shaking in the dark at 32° C. for 48 hours. The resulting culture broth was inoculated into a 3 L capacity fermentor containing 1.8 L of medium 3 and cultured under stirring at 32° C. at an aeration rate of 0.36 L/min and 400 rpm. After culturing for 40 hours while controlling the medium pH at 6.5 to 6.6 using sulfuric acid and sodium hydroxide, 0.210 g of levulinic acid, 8.1 g of glycine and 18 g of yeast extract were added to the medium and the culturing was continued by changing the aeration rate and the stirring speed to 0.72 L/min and 600 rpm, respectively, and controlling the medium pH at 6.3 to 6.4 using sulfuric acid and sodium hydroxide. A 8.1 g portion of glycine was added 12, 26 and 38 hours thereafter. The culturing was stopped 50 hours after the addition of levulinic acid. The amount of 5-aminolevulinic acid in the culture broth was 13 mM when measured by the method of Okayama et al. (*CLINICAL CHEMISTRY*, Vol. 36, No. 8, p. 1494, 1990). The average dissolved oxygen concentration in the culture broth after the addition of levulinic acid was 2.3 ppm. Also, the oxidation-reduction potential in the culture broth after the addition of levulinic acid shifted within the range of from 50 mV to 70 mV.

Example 11

The mutant strain CR-0072009 was inoculated into a 300 ml capacity baffled conical flask containing 50 ml of the medium 3 and cultured under shaking in the dark at 32° C.

for 48 hours on a rotary shaker. The resulting culture broth was inoculated into a 3 L capacity fermentor containing 1.8 L of the medium 3 and cultured under stirring at 32° C. at 0.36 L/min and 400 rpm. After culturing for 40 hours while controlling the medium pH at 6.5 to 6.6 using sulfuric acid and sodium hydroxide, 0.210 g of levulinic acid, 8.1 g of glycine and 18 g of yeast extract were added to the medium and the culturing was continued by changing the aeration rate and the stirring speed to 0.18 L/min and 200 rpm, respectively, and controlling the medium pH at 6.0 to 6.5 using sulfuric acid and sodium hydroxide. A 8.1 g portion of glycine was added 12 and 24 hours thereafter. The culturing was stopped 50 hours after the addition of levulinic acid. The amount of 5-aminolevulinic acid in the culture broth was 15 mM when measured by the method of Okayama et al. (*CLINICAL CHEMISTRY*, Vol. 36, No. 8, p. 1494, 1990). The dissolved oxygen concentration in the culture broth after the addition of levulinic acid was less than the detection limit. In addition, the oxidation-reduction potential in the culture broth after the addition of levulinic acid shifted within the range of from −220 mV to −180 mV.

As described in Example 7, the mutant strain CR-0072009 obtained by repeating mutation using *Rhodobacter sphaeroides* CR-002 as the parent strain is a strain which can produce 5-aminolevulinic acid on a markedly high concentration using inexpensive materials, such as glucose, glycine, and the like, so that it is possible to produce 5-aminolevulinic acid in an industrial scale by using this strain. In addition, as can be understood from the results of Examples 10 and 11, it is preferred to control the dissolved oxygen concentration in the culture broth at 2.0 ppm or less after the addition of levulinic acid, or the oxidation-reduction potential in the culture broth within the range of from −220 mV to 50 mV, in order to increase the productivity, and such a control can be effected easily by decreasing the stirring rotation speed.

Example 12

The mutant strain CR-0072009 was inoculated into each of three 300 ml capacity baffled conical flasks containing 50 ml of medium 3 and cultured under rotary-shaking in the dark at 32° C. for 48 hours. The resulting culture broth in one flask was inoculated into one of three 3 L capacity fermentor vessels containing 1.8 L of medium 3 and cultured at 32° C. The culturing was continued for 90 hours at an aeration rate of 0.36 L/min and a stirring speed of 400 rpm while controlling the medium pH at 6.5 to 6.6 with sulfuric acid and sodium hydroxide, except that the stirring rotation speed of one of the three vessels was changed to 250 rpm 25 hours after culturing. During the culturing, the dissolved oxygen concentration and 5-aminolevulinate synthase activity were measured. The 5-aminolevulinate synthase activity was measured as described below.

About a 30 ml portion of the culture broth was sampled and centrifuged to recover cells. The thus recovered cells were washed with a phosphate buffer (50 mM, pH 7.2), re-suspended in 5 ml of the same buffer, disrupted by a French press in the usual way and then centrifuged at 10,000×g for 30 minutes, and the thus obtained supernatant was used as a crude enzyme solution of 5-aminolevulinic acid synthase.

An enzyme reaction solution was prepared by adding 50 mM of glycine, 0.1 mM of pyridoxal phosphate, 1 mM of EDTA and 1.0 mg protein/ml of the above-described crude enzyme solution to 1 ml of a phosphate buffer (50 mM, pH 7.2). This was mixed with succinyl-CoA to give a final concentration of 0.2 mM and incubated at 37° C. After the incubation for 15 minutes, the reaction was stopped by adding 1 ml of 10 vol % trichloroacetic acid.

The reaction solution was centrifuged at 3,500 rpm for 10 minutes, 1 ml of the resulting supernatant was mixed with 2 ml of a 1 M acetate buffer (pH 4.7) containing 1% acetylacetone, and the mixture was allowed to react at 100° C. for 15 minutes and then rapidly cooled with ice. A 3.5 ml portion of Ehrlich's reagent was added thereto to measure, 15 minutes thereafter, the amount of the produced pyrrole compound based on the absorbance at 553 nm and to thereby calculate the produced amount of 5-aminolevulinic acid (a) by the enzyme reaction.

A formation rate of 5-aminolevulinic acid was calculated based on the following formula and used as the 5-aminolevulinic acid synthase activity. The relationship between the dissolved oxygen concentration in the culture broth and the 5-aminolevulinic acid synthase activity during the culturing is shown in FIG. 1 and Table 4.

Also, in FIG. 1, 10% dissolved oxygen concentration corresponds to 0.7 ppm, and 90% dissolved oxygen concentration corresponds to 6.6 ppm.

$$v = \frac{a}{t \times p}$$

v: enzyme activity (nmol/min/mg protein)

a: 5-aminolevulinic acid in 1 ml of enzyme reaction solution (nmol)

p: amount of protein in 1 ml of enzyme reaction solution (=1 mg)

t: reaction time (=15 min)

Comparative Example 1

The procedure of Example 10 was repeated, except that the strain was changed to CR-002. The results are shown in FIG. 1 and Table 4.

As is apparent from FIG. 1, inhibition of 5-aminolevulinate synthase activity, which is common in wild strains of photosynthetic bacteria, hardly occurs in the strain CR-0072009 even under such conditions that the dissolved oxygen concentration in the culture broth exceeds 2 ppm.

TABLE 4

| DO (%) | Example 12 | DO (%) | Comp. Ex. 1 |
|---|---|---|---|
| 0 | 6.7 | 0 | 5.5 |
| 0 | 9.2 | 0 | 7.6 |
| 0 | 7.3 | 20 | 0.6 |
| 1 | 7.1 | 50 | 0.5 |
| 20 | 4.7 | | |
| 23 | 4.1 | | |
| 23 | 4.2 | | |
| 49 | 3.7 | | |
| 50 | 5.2 | | |
| 75 | 4.9 | | |
| 76 | 3.5 | | |
| 79 | 5.6 | | |

Example 13

The following test was carried out using medium 3 used in Example 9, except that the yeast extract of the medium was changed to 5.0 g/L of yeast extract B manufactured by another manufacture (B-2, manufactured by Oriental Yeast).

In the same manner as in Example 9, the mutant strain CR-0072009 was cultured under stirring for 48 hours in a 300 ml capacity baffled conical flask, the resulting culture broth was inoculated into 1.8 L of medium 3 prepared using yeast extract B in a 3 L capacity fermentor and cultured at 32° C. with an aeration rate of 0.36 L/min and 400 rpm, and the culturing was continued by adding 0.210 g of levulinic acid, 8.1 g of glycine and 18 g of yeast extract B and by decreasing the stirring rotation speed to 325 rpm. After the addition of levulinic acid, the dissolved oxygen concentration remained at a level of 0.5 ppm for about 4 hours but started to increase after 5 hours. After 6 hours, it increased to 4 ppm and the production of 5-aminolevulinic acid stopped at 10 mM. When ferric chloride was added thereto to give a final concentration of 20 $\mu$M, the dissolved oxygen concentration was reduced again to 0.5 ppm or less and the production of 5-aminolevulinic acid started again within 2 hours after its addition, so that glycine was added in 8.1 g portions 12, 26 and 38 hours thereafter. The culturing was stopped 50 hours after the addition of levulinic acid. The amount of 5-aminolevulinic acid in the culture broth was 40 mM when measured by the method of Okayama et al. (*CLINICAL CHEMISTRY*, Vol. 36, No 8, p. 1494, 1990).

As is apparent from Example 13, the addition of an iron compound has the effect to recover respiration.

Reference Example 1

When examined by the ICP mass method, the amounts of iron in the yeast extract used in Example 9, yeast extract B used in Example 13 and another yeast extract C of other maker (Industrial Yeast Extract, manufactured by Oriental Yeast) used in the following examples were 73 $\mu$g, 25 $\mu$g and 155 $\mu$g, respectively, per gram of each yeast extract.

These results show that amounts of iron in medium 3 prepared using these yeast extracts are 6.64, 2.27 and 14.1 $\mu$M, respectively. Thus, it is found that 20 $\mu$M of iron is contained in the culture broth at the time of the production of 5-aminolevulinic acid in Example 9, and the medium of Example 13 contains 6.8 $\mu$M of iron before the addition of the iron compound and 26.8 $\mu$M after the iron addition.

Example 14

The mutant strain CR-0072009 (1 ml of culture broth obtained by culturing the strain for 48 hours using 10 ml of yeast extract C in a test tube of 21 mm in diameter (optical density at 660 nm, 0.2)) was inoculated into a 300 ml capacity baffled conical flask containing 50 ml of a medium prepared by adding 0.5, 10, 20, 50, 200 or 1,000 $\mu$M of ferric chloride to medium 3 in which its yeast extract had been replaced by 3 g/L of yeast extract C, and the strain was cultured under rotary-stirring in the dark at 32° C. When the iron component contained in the yeast extract is included, this medium contains the total iron content shown in Table 5. The results of the measurement of cell density as optical density at 660 nm 30 hours after culturing are also shown in Table 5.

TABLE 5

| Ferric chloride ($\mu$M) | Iron content ($\mu$M) | Cell density (optical density at 660 nm) |
|---|---|---|
| 0.5 | 8.4 | 10.3 |
| 10 | 13.4 | 12.5 |
| 20 | 28.4 | 16.3 |

TABLE 5-continued

| Ferric chloride ($\mu$M) | Iron content ($\mu$M) | Cell density (optical density at 660 nm) |
|---|---|---|
| 50 | 58.4 | 16.5 |
| 200 | 208.4 | 15.3 |
| 1000 | 1008.4 | 6.3 |

As apparent from Table 5, the addition of an appropriate amount of iron component has the effect to increase growth rate.

Example 15

The same volume of the mutant strain CR-0072009 described in Example 14 was inoculated into a 300 ml capacity baffled conical flask containing 50 ml of a medium prepared by adding 20 $\mu$M of ferric chloride to medium 3 in which its yeast extract had been replaced by 3 g/L of yeast extract C, and the strain was cultured under rotary-shaking in the dark at 32° C. for 48 hours. Portion of the resulting culture broth was inoculated into 1.8 L of the above-described medium in a 3 L capacity fermentor and cultured under stirring at 32° C., an aeration rate of 0.36 L/min, and 400 rpm. After culturing for 24 hours, 0.210 g of levulinic acid, 8.1 g of glycine and 9 g of yeast extract C were added to the medium, and the culturing was continued by decreasing the stirring rotation speed to 325 rpm and controlling the medium pH at 6.3 to 6.4 using sulfuric acid and sodium hydroxide. A 8.1 g portion of glycine was further added 12, 26 and 38 hours thereafter. The culturing was stopped 50 hours after the addition of levulinic acid. The amount of 5-aminolevulinic acid in the culture broth was 55 mM when measured by the method of Okayama et al. (*CLINICAL CHEMISTRY*, Vol. 36, No. 8, p. 1494, 1990). In this case, the average dissolved oxygen concentration in the culture broth after the addition of levulinic acid was 0.01 ppm. Also, the oxidation-reduction potential in the culture broth after the addition of levulinic acid shifted within the range of from −180 mV to −50 mV.

INDUSTRIAL APPLICABILITY

The microorganism of the present invention has excellent productivity of 5-aminolevulinic acid, and the 5-aminolevulinic acid production method using the microorganism does not require specific means, such as introduction of nitrogen gas or the like, even under conditions that the dissolved oxygen concentration is relatively high so that it can produce 5-aminolevulinic acid industrially advantageously.

What is claimed is:

1. A 5-aminolevulinic acid-producing microorganism having a 5-aminolevulinic acid synthase activity of from 2 to 7 (nmol/min/mg protein) under aerobic culture conditions having a dissolved oxygen concentration of from 0.70 to 6.60 ppm, wherein the microorganism is *Rhodobacter sphaeroides* or a mutant strain thereof.

2. The microorganism according to claim 1, wherein the microorganism is *Rhodobacter sphaeroides* CR-0072009 (FERM BP-6320) or a mutant strain thereof.

3. A process for producing 5-aminolevulinic acid, comprising culturing the 5-aminolevulinic acid producing microorganism of claim 1, and recovering 5-aminolevulinic acid from the resulting culture.

4. The process according to claim 3, wherein levulinic acid or glycine is added during the culturing.

5. The process according to claim 4, wherein the glycine is added at an amount of 200 mM or less per once.

6. The process according to claim 3, wherein the culturing is carried out at a dissolved oxygen concentration of from 0.001 to 2 ppm or at an oxidation-reduction potential of from −220 to 50 mV in the culture.

7. The process according to claim 3, wherein the 5-aminolevulinic acid-producing microorganism is cultured in a medium containing an iron component at an amount of from 5 to 500 μM.

8. The process according to claim 7, wherein the 5-aminolevulinic acid-producing microorganism has a 5-aminolevulinic acid synthase activity of from 2 to 7 (nmol/min/mg protein) under aerobic culture conditions having a dissolved oxygen concentration of from 0.70 to 6.60 ppm.

9. A process for culturing a 5-aminolevulinic acid producing microorganism, comprising culturing a 5-aminolevulinic acid producing microorganism in a medium containing an iron component at an amount of from 5 to 500 μM, wherein the 5-aminolevulinic acid-producing microorganism has a 5-aminolevulinic acid synthase activity of from 2 to 7 (nmol/min/mg protein) under aerobic culture conditions having a dissolved oxygen concentration of from 0.70 to 6.60 ppm, wherein the microorganism is *Rhodobacter sphaeroides* or a mutant strain thereof.

10. The process according to claim 3, wherein the microorganism is *Rhodobacter sphaeroides* CR-0072009 (Deposition No.: FERM BP-6320) or a mutant strain thereof.

* * * * *